United States Patent [19]

O'Brien et al.

[11] Patent Number: 5,313,047
[45] Date of Patent: May 17, 1994

[54] ANALYTICAL SAMPLE PREPARATION SYSTEM

[75] Inventors: Larry S. O'Brien; Gordon C. Ford, both of St. Joseph; Peter M. Willis; Ronald A. Klemm, both of Benton Harbor, all of Mich.

[73] Assignee: Leco Corporation, St. Joseph, Mich.

[21] Appl. No.: 25,228

[22] Filed: Mar. 2, 1993

Related U.S. Application Data

[63] Continuation-in-part of Ser. No. 846,814, Mar. 6, 1992, Pat. No. 5,277,493, which is a continuation-in-part of Ser. No. 664,052, Mar. 1, 1991, Pat. No. 5,269,827.

[51] Int. Cl.$^5$ ............................................. F27B 17/02
[52] U.S. Cl. ............................ 219/385; 219/420; 219/424; 219/415; 219/422; 219/531; 373/118; 432/262; 432/156; 164/338.1
[58] Field of Search ............... 219/385, 420, 424, 456, 219/421, 531, 425, 426, 422, 415–417; 373/118, 115; 432/262, 162, 156, 210, 157, 243, 239, 93; 266/276, 275, 242; 65/347, 335, 355, 275, 259, 242, 347; 164/335, 136, 338.1, 250.1, 4.1, 48, 492; 425/DIG. 13

[56] References Cited

U.S. PATENT DOCUMENTS

| | | | |
|---|---|---|---|
| 1,485,151 | 2/1924 | Roessel et al. | 432/210 |
| 2,003,714 | 6/1935 | Johnson | 219/460 |
| 2,171,778 | 9/1939 | Yantis | 164/335 |
| 2,180,602 | 11/1939 | Morgan | 219/460 |
| 2,190,135 | 2/1940 | Morgan et al. | 219/421 |
| 2,798,932 | 7/1957 | Evans | 219/44 |
| 2,804,777 | 9/1957 | Kerr-Lawson | 74/42 |
| 3,437,317 | 4/1969 | Micin | 259/75 |
| 3,451,794 | 6/1969 | Patterson | 65/18 |
| 3,619,839 | 11/1971 | Kraus et al. | |
| 3,630,480 | 12/1971 | Inouye | 164/335 |
| 3,712,364 | 1/1973 | Daniel et al. | 164/338.1 |
| 3,757,961 | 9/1973 | Jacobs | 214/1 BB |
| 3,798,418 | 3/1974 | Reik et al. | 219/460 |
| 3,890,089 | 6/1975 | Matocha | 432/11 |
| 3,936,587 | 2/1976 | Sitek et al. | |
| 4,045,202 | 8/1977 | Claisse | 65/178 |
| 4,072,814 | 2/1978 | Boillot | |
| 4,138,209 | 2/1979 | Bahr | 425/160 |
| 4,317,560 | 3/1982 | Troyer | 266/48 |
| 4,328,386 | 5/1982 | Bredeweg | 373/118 |
| 4,329,136 | 5/1982 | Willay | 425/174.8 |
| 4,419,754 | 12/1983 | Sitek et al. | 373/118 |
| 4,562,337 | 12/1985 | Lawrence | 219/421 |
| 4,563,146 | 1/1986 | Kelly et al. | 425/256 |
| 4,609,392 | 9/1986 | Claisse | 65/134 |
| 4,871,309 | 10/1989 | Chapman | 432/156 |
| 5,055,263 | 10/1991 | Meltzer | 422/65 |
| 5,167,928 | 12/1992 | Kelly et al. | 422/99 |

FOREIGN PATENT DOCUMENTS

| | | |
|---|---|---|
| AUB23693/-88 | 2/1989 | Australia . |
| 3025210 | 1/1982 | Fed. Rep. of Germany . |
| 2248479 | 5/1975 | France . |
| 1527321 | 10/1978 | United Kingdom . |

OTHER PUBLICATIONS

"Look to the leader, in Claisse Fluxer-Bis!," Corporation Scientifique Claisse, Inc.

Primary Examiner—Bruce A. Reynolds
Assistant Examiner—John A. Jeffery
Attorney, Agent, or Firm—Price Heneveld Cooper DeWitt & Litton

[57] ABSTRACT

An interchangeable module for supporting a receptacle into which a molten sample, prepared by a fluxer, can be poured for analysis. One module can support a resistively heated casting dish into which a molten sample can be poured and cooled to form a solid sample for instrumental analysis. This module includes an insulator having a depression for receipt of a casting dish. A heating coil is positioned below the recession. A cooling gas conduit extends through the insulator support. The insulator is supported on a frame. The frame is supported on a back plate.

12 Claims, 9 Drawing Sheets

ANALYTICAL SAMPLE PREPARATION SYSTEM

CROSS-REFERENCE TO RELATED APPLICATION

The present application is a continuation-in-part of application Ser. No. 07/846,814 filed Mar. 6, 1992, now U.S. Pat. No. 5,277,493, entitled ANALYTICAL SAMPLE PREPARATION SYSTEM which, in turn, is a continuation-in-part of application Ser. No. 07/664,052 filed Mar. 1, 1991, now U.S. Pat. No. 5,269,827, also entitled ANALYTICAL SAMPLE PREPARATION SYSTEM. The present application is assigned to the assignee of both of the above applications.

BACKGROUND OF THE INVENTION

The apparatus of the present invention is commonly referred to as a "fluxer." In this type of apparatus, a sample is heated to a molten state in a crucible and is then either poured into a casting dish to prepare a solid glass-like disc for analysis by instrumental techniques or the heated sample is poured into an acid solution contained in a beaker for analysis. Some of the devices known in the past would add materials to the crucibles while the crucibles were above and being heated by the burners. Also, the molten contents of the crucible was poured into a casting dish above the burner, the burner being used to heat the crucible and the casting dish. A fluxer usually contained several burners and facilities for supporting several crucibles. If the apparatus was prepared to add a wetting agent to the molten sample in the crucible, and a crucible was not in place, the wetting agent could be dumped directly into the burner. Likewise, if the laboratory technician forgot to install a casting dish into the apparatus and the apparatus dumped the contents of the crucible into the absent casting dish, the contents would be poured into the burner. In either case, the burner would be seriously damaged or totally destroyed by the molten material.

It is also known in the operation of a fluxer that the crucible should be agitated vigorously in order to properly mix the molten sample in the crucible. Various complicated mechanical arrangements have been provided for moving the crucible while it is being heated and, in some cases, a shaped crucible was used to cause the material to separate and remix as it was poured from one side of the crucible bottom to the other.

In order to form a solid sample suitable for X-ray or other analytical techniques, it was necessary to heat the casting dish to a high enough temperature, preferably to the melting range of the sample, so that the sample could be poured from the crucible into the casting dish without undergoing thermal shock. The casting dishes were usually heated by gas burners which added a substantial amount of heat and combustion products to the fluxer enclosure.

For wet chemical analysis, using an aqueous acid solution, it was the usual procedure to employ magnetic stirring with each beaker being driven by its own motor. The extensive wiring required for the separate stirring motor further added to the complexity and cost of the fluxer.

SUMMARY OF THE INVENTION

In accordance with the present invention, an improved fluxer is provided employing interchangeable modules for handling a casting dish or a magnetically stirred container of aqueous acidic solution.

The module for handling a casting dish has a frame for supporting an insulating material which has a configured upper surface for supporting a casting dish. An electric resistive heater is positioned in said insulating material to supply heat directly to a casting dish. Electrical conductors are provided on the module for supplying electric power to the resistive heating element and a conduit is provided for supplying cooling air to a heated casting dish.

The interchangeable module for providing stirring for a solution into which a molten sample can be poured has a supporting frame covered by a metal enclosure. The supporting frame has a horizontal surface upon which a rotatably mounted, horizontally disposed driven gear is mounted. A driving gear is operatively coupled to said driven gear. An electric motor is operatively coupled to said driving gear for rotating the driving gear and the driven gear. An upstanding clip member is centrally located on said driven gears for supporting a permanent magnet.

DETAILED DESCRIPTION OF THE PREFERRED EMBODIMENTS

Figure 1:
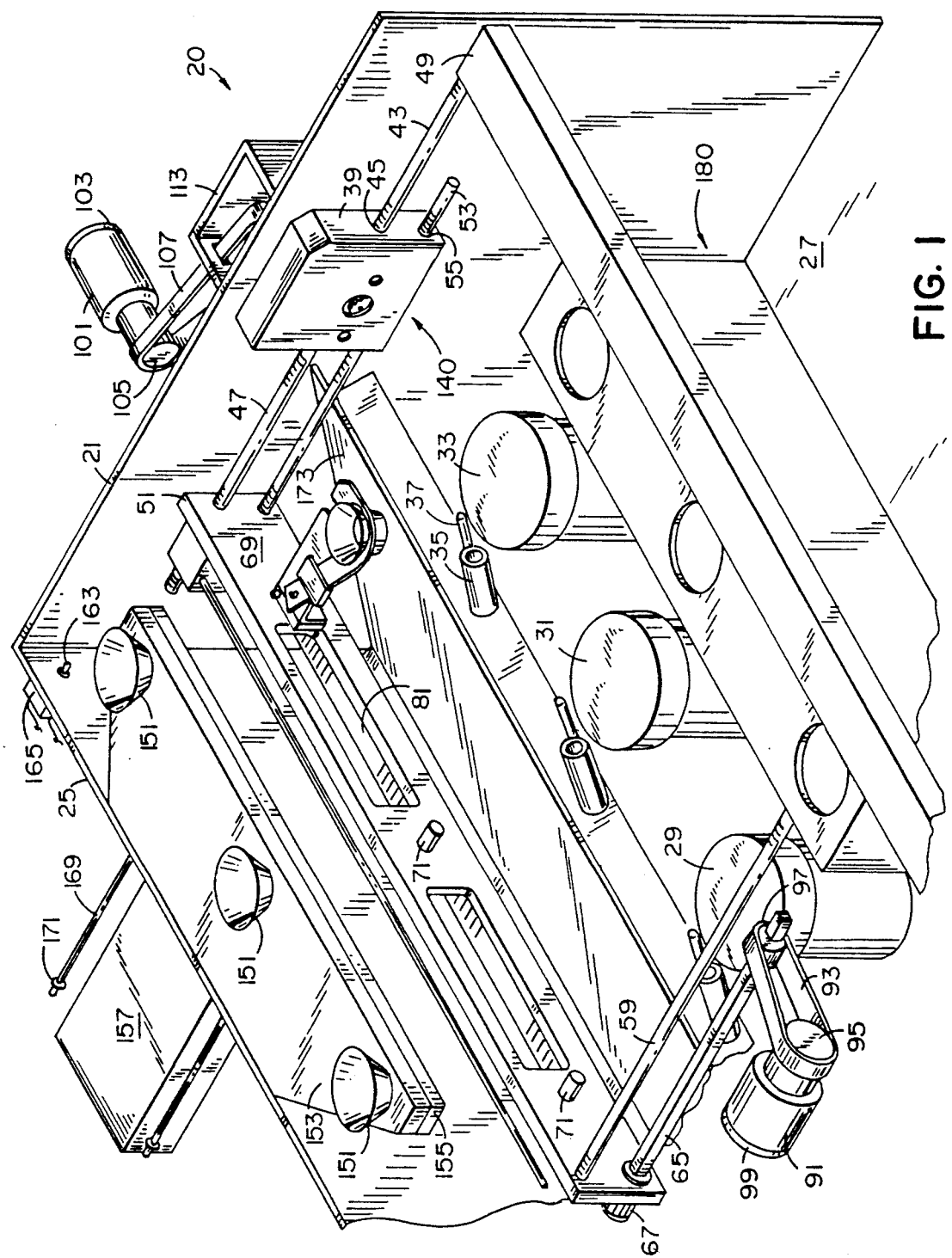
FIG. 1 is a fragmentary perspective view of the apparatus showing the main components.

The improved fluxer of the present invention is indicated by the number 20. The apparatus has an open front, a right sidewall 21, a left sidewall 23, a back wall 25 which is connected to the right and left sidewalls, and a bottom plate 27. Three burners 29, 31 and 33 extend upwardly from bottom plate 27. Each burner has an igniter 35 and a thermocouple 37 for lighting and monitoring the temperature of the associated burner.

A first journal block 39 is pivotally mounted on the inside surface of sidewall 21. A second journal block 41 is pivotally mounted on the inside surface of left sidewall 23, the pivot for journal block 41 being obscured by chain 93. An elongated shaft 43 is slidably mounted in an upper aperture 45 in journal block 39. Shaft 43 has a rack gear pattern 47 on its upper surface. Shaft 43 supports a counter balance 49 at one end and a movable subframe 51 on the opposite side of journal block 39 from counter balance weight 49. A second rack 53 extends through aperture 55 in journal block 39. Rack 53 is fastened to movable subframe 51. A pinion gear 57 causes rack 53 to move and, in turn, the subframe to move.

Journal block 41 is pivotally mounted on the inside of sidewall 23, the pivot point is obscured by a continuous chain. A shaft 59, similar to shaft 43, extends through journal block 41 and is fastened to counter balance 49. Shafts 43 and 59 are fastened to counter balance 49 by a pair of fastener members 61 and 63. A second shaft 65 is also supported in journal block 41. Shaft 65 is preferably square in configuration. A driving gear 67 is mounted on the end of shaft 65 behind front panel 69 of movable subframe 51. Subframe 51 has a front panel 69 which supports three movable shafts 71. Shafts 71 are mounted in bushings 73. Because of the heat involved in the operation of the machine, the components are made of stainless steel with the exception of the bushings which are bronze. Shafts 71 support crucible holders 75 which are clamped to shafts 71 by threaded fasteners 77.

Behind panel 69 each shaft 71 supports a sprocket 79. A continuous chain 81 is trained over driving gear 67 and each of sprockets 79.

A pair of journal blocks 83 are mounted on the back of panel 69. A cross shaft 85 is supported by each of the journal blocks. Cross shaft 85 has a pinion gear 87 attached to each end. Pinion gears 87 mesh with the rack-like teeth on the top of shafts 43 and 59 and prevent subframe 51 from cocking or canting as it is moved backward and forward by rack 53 and pinion gear 57.

A first drive motor 91 is operatively connected to square shaft 65 by a continuous chain 93 which is trained over a sprocket 95 on motor 91, and a sprocket 97 mounted on square shaft 65. A shaft encoder 99 is coupled to motor 91. Motor 91 is preferably a servo motor and the shaft encoder provides output pulses or counts indicating the motion of sprocket 95 on the output of motor 91. Motor 91 causes sprocket gear and square shaft 65 to oscillate which, in turn, causes driven gear 67 to oscillate. Driven gear 67 is connected to sprockets 79 on the end of each of the shafts 71 which causes shafts 71 to oscillate as chain 81 moves back and forth over the sprockets. Shafts 71 support the holders for the crucibles.

A second motor 101 is mounted on the outside of sidewall 21. Motor 101 is preferably a servo motor and has a shaft encoder 103 which provides a pulse for each step of the rotation of the motor. A sprocket 105 is attached to the output of motor 101. A continuous chain 107 is trained over sprocket 105 and a sprocket 109 in clutch assembly 110. Sprocket 109 is mounted on a shaft 111 upon which pinion gear 57 is mounted.

Figure 5:
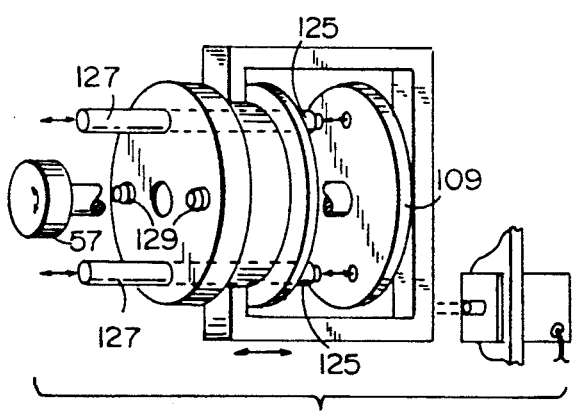
FIG. 5 is a partial broken away view of the clutch assembly.
Figure 6:
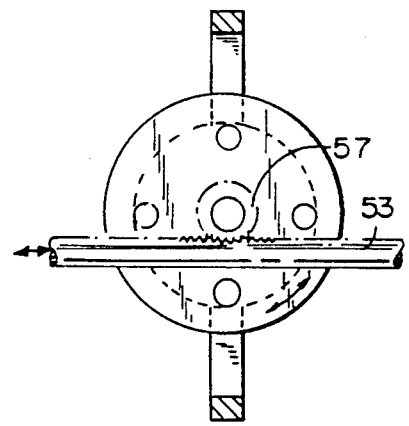
FIG. 6 shows the movement of the clutch disc for moving the junction block and the pinion gear.
Figure 7:
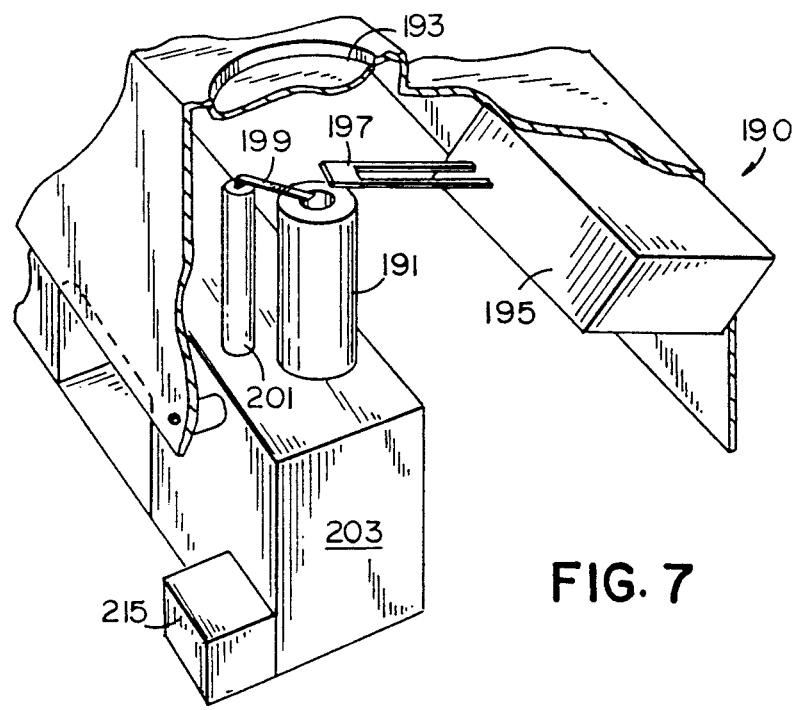
FIG. 7 is a fragmentary perspective view of the casting dish subassembly.
Figure 8:
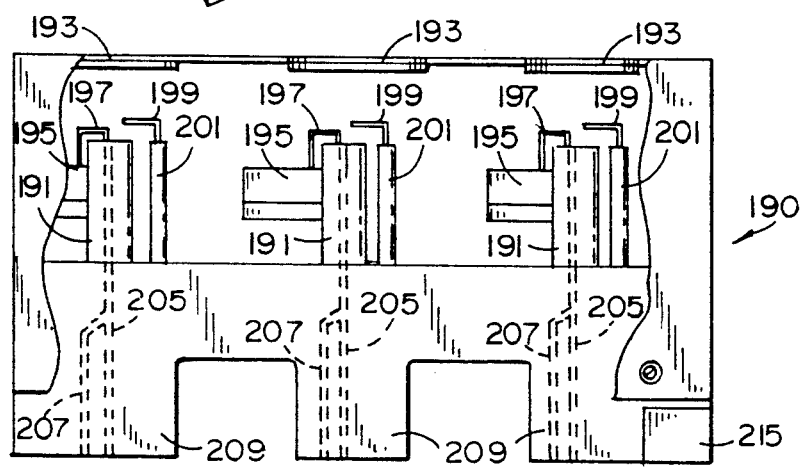
FIG. 8 is an elevational view of the casting dish subassembly.
Figure 9:
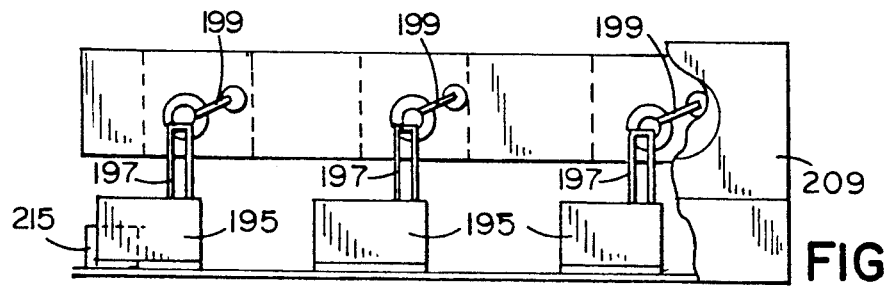
FIG. 9 is a top plan view of the casting dish subassembly.

Clutch assembly 110 has an outer frame 113 (FIGS. 2, 3 and 5) which attaches the clutch assembly to the outside of sidewall 21. Within frame 113 a substantially C-shaped movable member 115 is mounted. A pneumatic cylinder 117 is connected by a shaft 119 to movable member 115. Movable member 115 has a pair of opposed gripping faces 121 which grip clutch member 123.

Clutch member 123 is made of brass and supports two sets of steel pins. A first set of pins 127 are for connecting clutch 123 to sprocket gear 109. When so connected, pins 127 positioned in apertures 126 in journal block 39 cause the journal block to oscillate as determined by servo motor 101. When the clutch plate moves to the left, as shown in the figures, the second pin 129 enters apertures 131 on the outside of sidewall 21 which locks the clutch assembly, preventing any further movement of the frame and journal blocks 39 and 41. Sprocket gear 109 and shaft 111 can now rotate pinion 57 to cause subframe 51 to move forward or backward in the apparatus.

Journal blocks 39 and 41, shafts 43 and 59, counter balance 49 and movable subframe 51 make up a major movable frame 140. Frame 140 can oscillate vertically to mix the components in the crucible and can be locked in a horizontal position so that the subframe 51 can move to the rear of the apparatus for the addition of materials to the crucibles, or toward the front of the apparatus so that the contents of the heated crucibles can be poured into either a casting dish or a beaker containing an acid solution for analysis.

First servo motor 91 and second servo motor 101 combine to cause the main frame 140 to oscillate up and down while the crucibles supported by shafts 71 are rocking back and forth in a horizontal plane. The extent of the vertical and horizontal motion applied to the crucibles can be varied by monitoring the shaft encoders 99 and 103 so that the motors 91 and 101 undergo either large or small excursions before stopping and reversing travel. Motors 91 and 101 can be controlled by the overall program for the operation of the machine, as set forth in the parent application, all of which is incorporated herein by reference.

Figure 19:
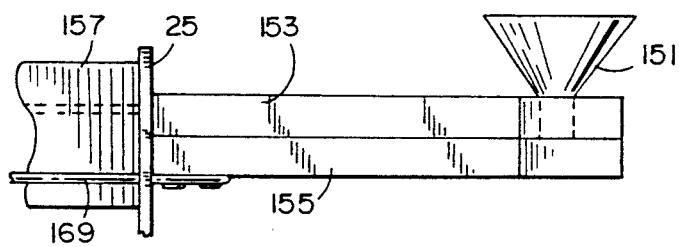
FIG. 19 is an elevational view of the apparatus used to add additional materials with the funnels closed.
Figure 20:
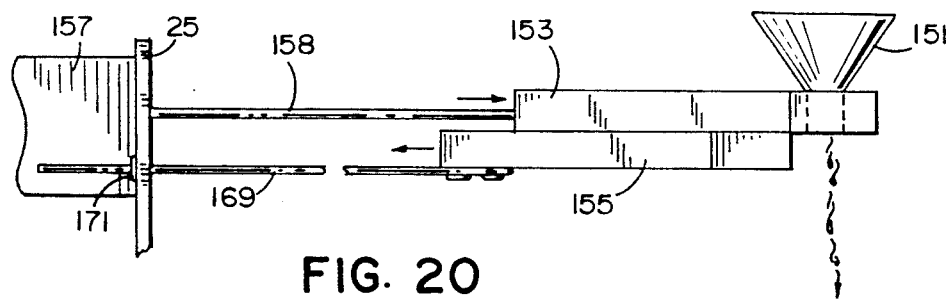
FIG. 20 is a view of the apparatus of FIG. 19 extended and with the funnel bottom opened.

It is common practice in the preparation of a sample for further analysis to add a wetting agent to the molten material contained in the crucibles. In the present apparatus, the wetting agents can be added to funnels 151 which are movably supported near the top of back wall 25 of the apparatus. The material addition apparatus includes an upper plate 153 which is in sliding contact with a lower plate 155. Funnels 151 have an open bottom (FIGS. 19 and 20) which is closed off by lower plate 155. A double pneumatic cylinder 157, which has a dual extending piston 158, only one of which is shown, is attached to upper plate 153. Lower plate 155 is carried by upper plate 153. Upper plate 153 has a plurality of spaced slots 159 in which a large-headed fastener 161 is attached to lower plate 155. Fasteners 161 hold lower plate 155 in tight sliding contact with upper plate 153.

As mentioned previously, movable subframe 51 can be caused to move to the rear of the machine to move the crucibles away from the burners for the addition of additives to the crucible. As the subframe moves toward the rear of the machine, it contacts a pin 163 in valve 165 which actuates double pneumatic cylinder 157 through line 167. Valve 165 functions, in effect, as an interlock and will not allow plates 153 and 155 to move until valve 165 has been opened, indicating that subframe 51 and the supported crucibles are at the rear of the apparatus. Once valve 165 is activated, dual pneumatic cylinder 157 moves plates 153 and 155, along with funnel 151 containing the additive material. Rods 169 are attached to the rear edge of lower plate 155. Each rod 169 has a stop 171 mounted thereon which stops the movement of plate 155, enabling plate 153 to continue to be driven forward, moving the bottoms of funnels 151 away from plate 155 and enabling the material contained in the funnels to drop into the heated crucibles. A heat shield and deflecting plate 173 extends across the width of the apparatus to prevent any possibility of any of the additive material, or any of the material in the crucible, from accidentally landing on any wiring or plumbing. Slots 159 in plate 153 enable plate 153 to be driven beyond plate 155 to enable the bottoms of the funnels to be opened in a gate valve-like manner.

After the wetting agent is added to the crucibles, subassembly 51 is moved forward to return the crucibles over burners 29, 31 and 33. After the crucible is reheated, subframe 51 moves forward bring the heated crucibles to the output station 180 where the molten material can either be poured into a casting dish to prepare a glass-like disc for analysis, or into a beaker containing an acid solution for further analysis.

At output station 180 plug-in modules 190, 220, 260 or 330 can be mounted. Plug-in assembly 190 has three burners 191 for heating casting dishes 193 to prevent the sample material from being damaged by thermal shock on pouring from a hot crucible into a cold casting dish. Each burner 191 has its own electrical igniter 195 which has a hot loop 197 extending out over the burner to ignite the combustion mixture of air and gas. Each burner has a flame detection wire 199 supported on an insulated post 201 for monitoring the status of the flame for heating casting dish 193. Burners 191 and flame detection supports 201 are supported on a solid frame 203 which has internal passages 205 and 207 for the air and fuel used in the burner. The passages for the air and gas are contained within spaced leg portions 209 of frame 203. Ports 211 and 213 are provided on the bottom of each leg 209 for connecting to the supply of air and gas in the apparatus. An electrical connector 215 is also provided on the plug-in assembly which connects the power source for igniters 195 and connects flame detectors 199 to the apparatus. The electrical plug 215 also contains circuitry to indicate to the control system of the apparatus that the casting dish assembly is in position and that the solenoid valves for the air and gas can be activated.

Figure 13:
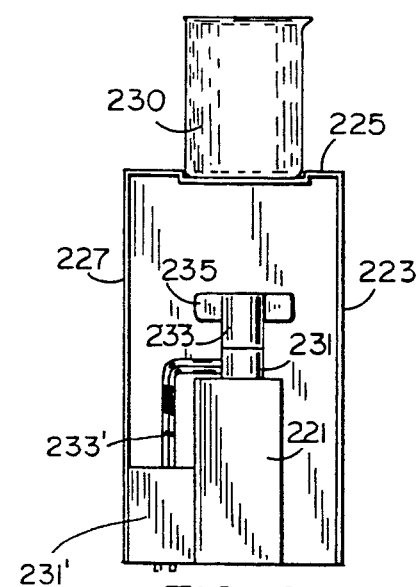
FIG. 13 is a side elevational view of the acid solution subassembly.
Figure 14:
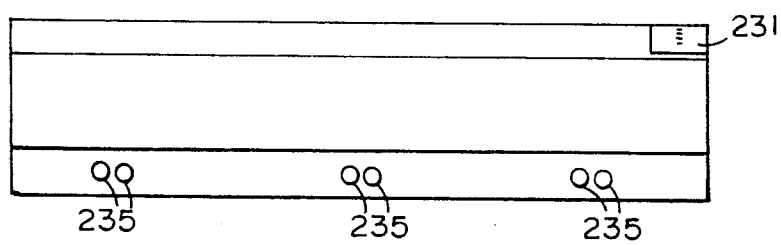
FIG. 14 is a bottom plan view of the acid solution subassembly.
Figure 12:
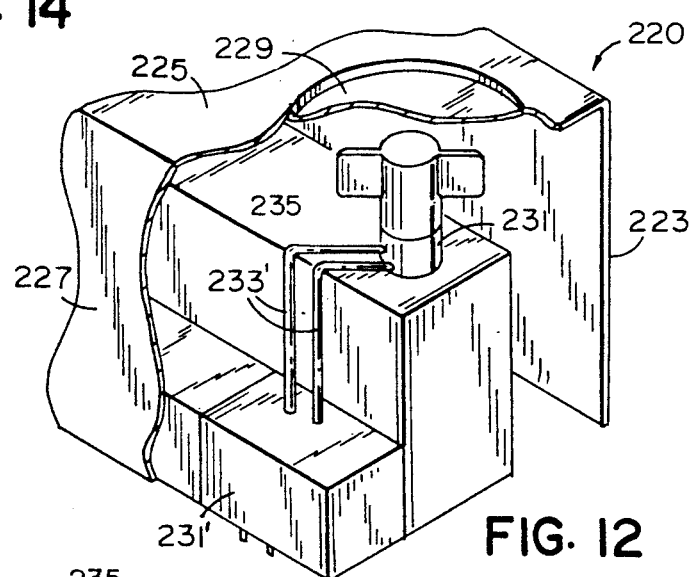
FIG. 12 is a fragmentary perspective view of the subassembly used with an acid solution.
Figure 15:
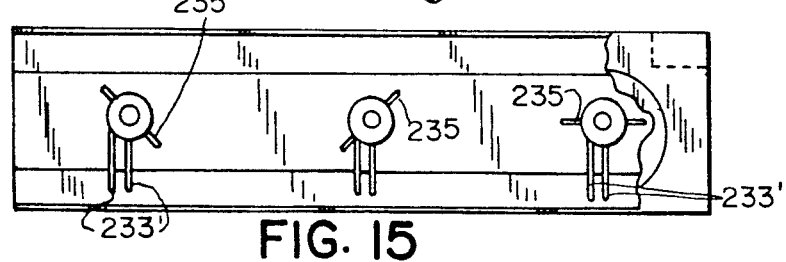
FIG. 15 is a top plan view of the acid solution subassembly.

When the molten sample in the crucible is to be poured into a beaker containing an acid solution, separate subassembly 220 can be inserted into the apparatus. Subassembly 220 has a base 221 (FIG. 13) which supports a vertical metal plate 223 which has a turned-over top section 225 and a downwardly turned edge 227. Top surface 225 has spaced recessed portions 229 for centering a beaker 230 over electric motor 231 which has an output shaft 233 supporting a bar magnet 235. The bottom of recess 229 is preferably made of a magnetic permeable material, such as stainless steel. The stainless steel will permit the magnetic field from the rotating bar magnet to act along with a bar magnet contained in the beaker to stir the solution. The plug-in assembly has an electrical connector 231' for providing power through electrical conductors 233' for driving magnetic stirring motor 231. The assembly also has plugs 235' for closing off the air and combustible gas inlets to the subassembly. When electrical plug 231' is connected to the apparatus, the connections in plug 231' enable the apparatus to determine that the magnetic stirring motors are in position, that the air and gas solenoids are not to be activated, and that the thermocouple and igniter circuits are disconnected.

Figure 21:
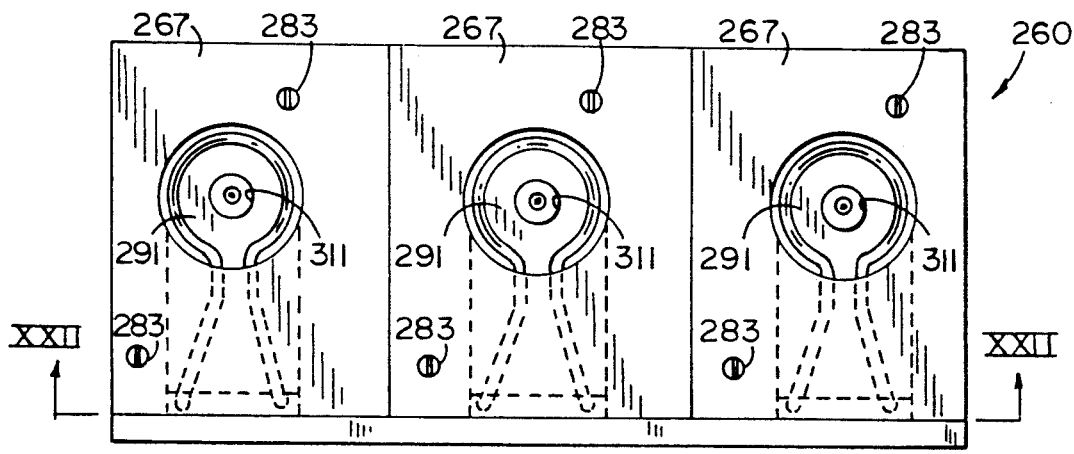
FIG. 21 is a plan view of the resistively heated casting dish support.
Figure 22:
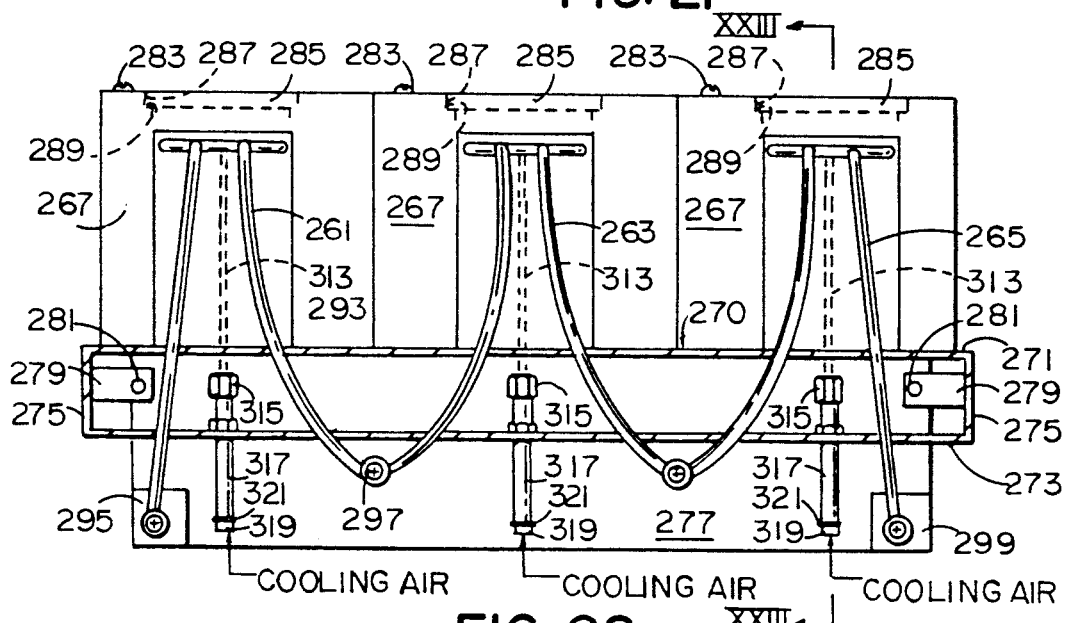
FIG. 22 is a sectional view of the casting dish support taken in the direction of line 22—22 of FIG. 21.
Figure 23:
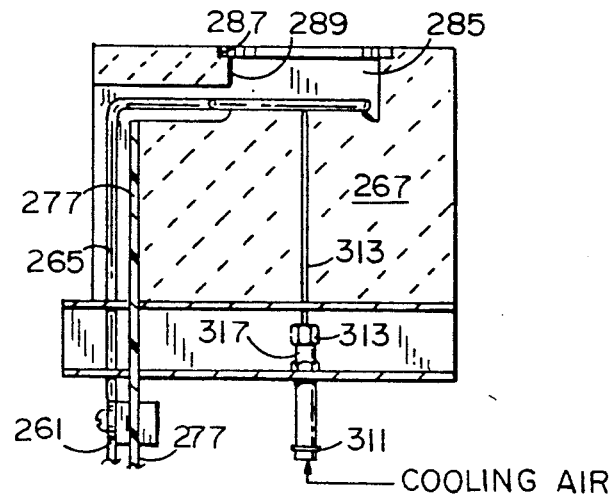
FIG. 23 is a side elevational view showing the configuration of the resistive heating element.

In order to reduce the amount of extraneous heat and combustion products produced inside the fluxer, an electrical resistance heated module 260 can be used in lieu of module 190. Referring to FIGS. 21-23, module 260 is shown having three electrical heating elements 261, 263 and 265. Three elements are shown to be consistent with the three main burners used in the fluxer. In situations where more or less main burners are used, more or less casting dish support heaters can be used.

Each of the electrically energized casting dish heaters has a supporting block of electrical and thermal insulating material 267 which is preferably a mixture of a glass fiber and a ceramic powder material. The fibrous ceramic molded material is available from Leco of Augusta, Ga. The material is very light in weight and has excellent insulating properties. The three blocks of insulating material, as shown in the figures, are attached to the upper surface of a substantially rectangular box-like supporting frame 270. Frame member 270 has an upper shelf 271 and a lower shelf 273 joined by spaced end members 275 to form a substantially rectangular open box. A sheet of electrically insulating material 277 is attached to brackets 279 at each end of the box-like frame by fasteners 281. Insulating sheet 277 covers one face of frame 270 and extends below the frame in order to raise the upper surface of the insulating blocks to the same level of casting dish support 190. Insulating blocks 267 are attached to the top surface 271 of frame 270 by a plurality of threaded screws 283 which extend downward through the insulating blocks into threaded apertures (not shown) in top surface 271.

Each of the electrical resistance heating elements 261, 263 and 265 are made of molybdenum disilicide which is obtained from Kanthal Corporation of Bethel, Conn. The electrodes are preferably bent to the shape of a lower depression 285 in the upper surface of insulating blocks 267. An upper depression 287 is substantially coaxially aligned with lower depression 285 and has a circumferential shelf 289 for supporting the casting dish directly above the heating element. The configuration of the insulation tends to limit the amount of extraneous heat released to the interior of the fluxer while, at the same time, causing the radiant energy from the heaters to be directed upwardly at the bottom of each casting dish. The resistive heating elements provide more uniform heating of the casting dish. Also, the casting dishes can reach a higher temperature with less energy because of the insulation surrounding the heating elements. A distinct advantage of the electric resistive heating module 260 over gas heated module 190 is that the casting dishes can cool more quickly since there is less thermal mass to cool. Also, the potential safety problems associated with a combustible gas are eliminated by the safer low voltage heating elements.

The resistive heating elements are connected in series by electrical conductors 293. Electrical resistive heating element 261, for example, is connected to an electrical connector block 295 by electrical conductor 293. The other end of heating element 261 is connected again by a conductor 293 to a stud 297 attached to insulated support panel 277. In a similar manner, electrical conductors 263 and 265 are connected until the end of conductor 265 is connected to an electrical connector block 299.

Figure 27:
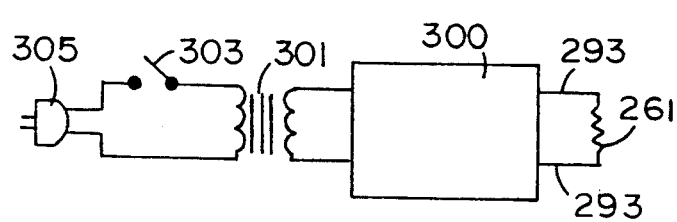
FIG. 27 is a schematic, in block diagram form, of the electrical connections to a resistive heater.

Referring to FIG. 27, the electrical heating elements 261-263 are represented by a single resistor which is connected by conductors 293 to a soft start module 300 whose input is attached to the output of transformer 301 which is connected by a plug 305 to a conventional outlet or source of electrical energy. The resistive heating elements exhibit practically zero resistance at turn-on. In order to control the flow of current through the heating elements, the elements are connected through the soft start block 300 to the transformer 301. Soft start block 300 contains a conventional circuit which slowly increases the width of each pulse of the input AC signal applied to the resistor until the resistor has developed, through thermal heating, sufficient internal resistance to have the full power applied. Transformer 301 is a step-down transformer which has a primary receiving the 120 volt input voltage which is stepped down to 7 volts at approximately 100 amps.

Figure 10:
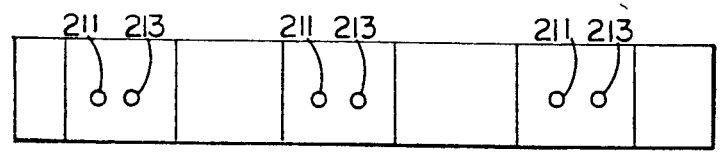
FIG. 10 is a bottom plan view of the casting dish assembly.
Figure 11:
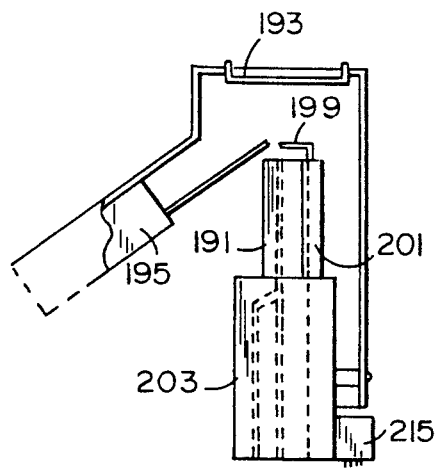
FIG. 11 is a side elevational view of the casting dish subassembly.

Each insulating block 267 has a vertical aperture 311 disposed substantially at the center of the area bounded by the resistive heating element 261. A small air conduit 313 extends upwardly through the aperture and terminates at a point just below the electrical heating element. Conduit 313 is connected to a reducer coupling 315 which is attached to the end of an enlarged tubular member 317 which has a shaped end 319 for plugging into port 211 (FIG. 10) from which a supply of air can be obtained. An O-ring 321 is positioned in a circumferential groove about the end portion of the tube to provide an air-tight seal when the tube is inserted into port 211. The enlarged tube 317 is attached to lower shelf 273 of the frame by a compression nut 325, or other suitable fastener, to hold the tube rigidly in place. Air conduit 313 is used to provide a stream of cool air to the bottom of a heated casting dish to controllably remove heat from the casting dish during the solidification of the molten sample.

When plug-in electrical resistance module 260 is employed, the gas previously supplied to module 190 can be shut off. The radiant heat supplied by resistive heaters 261-265 can be restricted by the depressions in the upper surface of insulating blocks 267 so that it is directly applied to the bottom of the casting dish without being spread out supplying unnecessary heat to the fluxer environment. By eliminating the gas flames, the amount of combustion products is also reduced eliminating the amount of fumes generated by the fluxer when in operation. The electric resistance heaters also enable the heating time for the casting dishes to be substantially reduced. The heaters can be energized to heat the casting dishes shortly before the molten sample is poured into the casting dish and can then be turned off after the sample has been poured to enable the sample to cool and form a glass-like bead within the casting dish.

When the molten sample is to be poured into an acid solution contained within, for example, a beaker, it is preferred to use the module 330 to replace the module 220. Each stirring position in module 220 employs a separate electric motor which requires additional wiring to bring the electric current to a jack to which the module is connected. This unnecessarily complicates the stirring assembly and also the wiring in the fluxer. In view of the extremely high temperatures generated in the fluxer, the fewer components exposed to this heat the better.

Stirring module 330 has three stirring positions to be consistent with the three main burners shown in the fluxer. The number of stirring positions can be increased or decreased to correspond to the number of heating positions.

Figure 24:
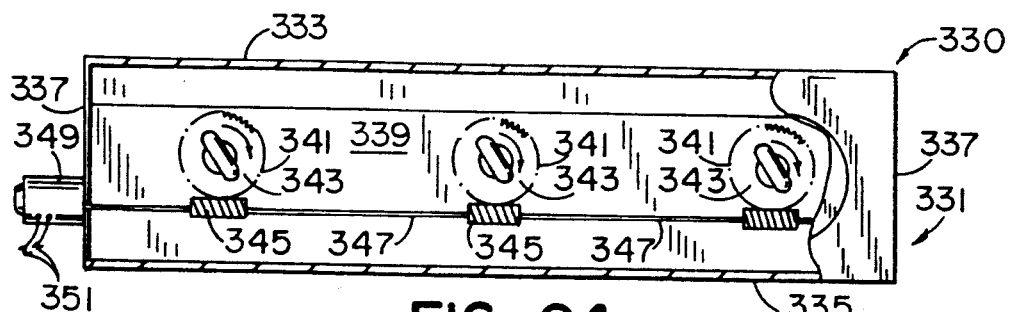
FIG. 24 is a plan view of the magnetic stirring module.
Figure 25:
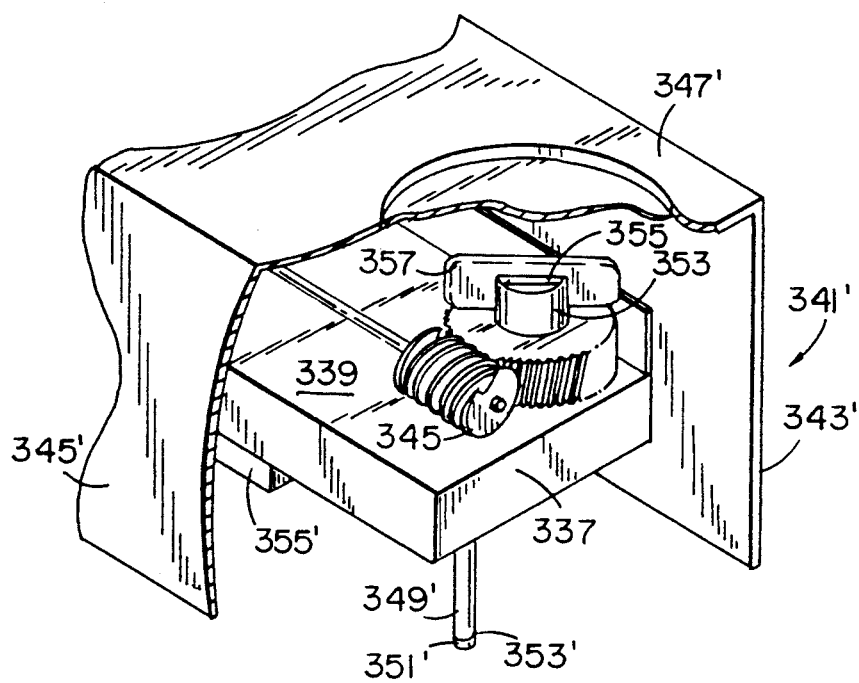
FIG. 25 is a partial perspective view of the stirring module.

Referring to FIGS. 24 and 25, a supporting frame 331 is shown which has spaced side members 333 and 335 joined by end members 337 to form a substantially box-like supporting frame having a substantially horizontal upper surface 339. Spaced across surface 339 are three stirring positions 341, each of which has a rotatably mounted horizontally disposed worm gear 343 which is driven by a worm 345. The worms 345 are connected together by a shaft 347 which is connected to the output of a single electric motor 349 which is attached to the end of frame 331 and supplied with electrical energy through conductors 351. Electric motor 349, the only electric motor used to drive all of the stirrers, can be a fractional horse power motor.

Figure 26:
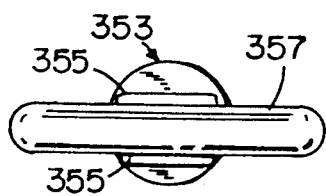
FIG. 26 shows a clip on the worm gear holding the bar magnet.

Referring to FIGS. 25 and 26, a clip member 353 is centrally positioned on the top of each worm gear 343. Clip 353 has a pair of opposed gripping faces 355 for grasping each side of a Teflon coated permanent magnet 357. Clip member 353 can be made of spring steel or brass and can be attached to worm gear 343 by a suitable fastener such as a screw, bolt or rivet.

Stirring assembly 330 is preferably covered by a box-like stainless steel shell 341. Side member 337 of frame 331 is attached to the inner surface of shell 341 by suitable fasteners, not shown. Cover 341 has a pair of vertically upstanding side portions 343 and 345 which support the upper surface 347 at the same height as the upper surface of module 220. A plurality of plug members 349 (only one of which is shown) are attached to the bottom of frame 331 and have shaped ends 351 with surrounding O-rings 353 for insertion into ports 211 which are used to locate the module. Posts 349 support the rear portion of the stirring module. A connector block 355 is attached to the bottom of the stirring module into which a suitable plug can be inserted to provide electrical power for motor 349.

Stirring module 330 substantially reduces the electrical complexity of the fluxer apparatus and eliminates two electric motors. The simplicity of the improved module substantially increases the dependability and durability of the module.

Figure 16:
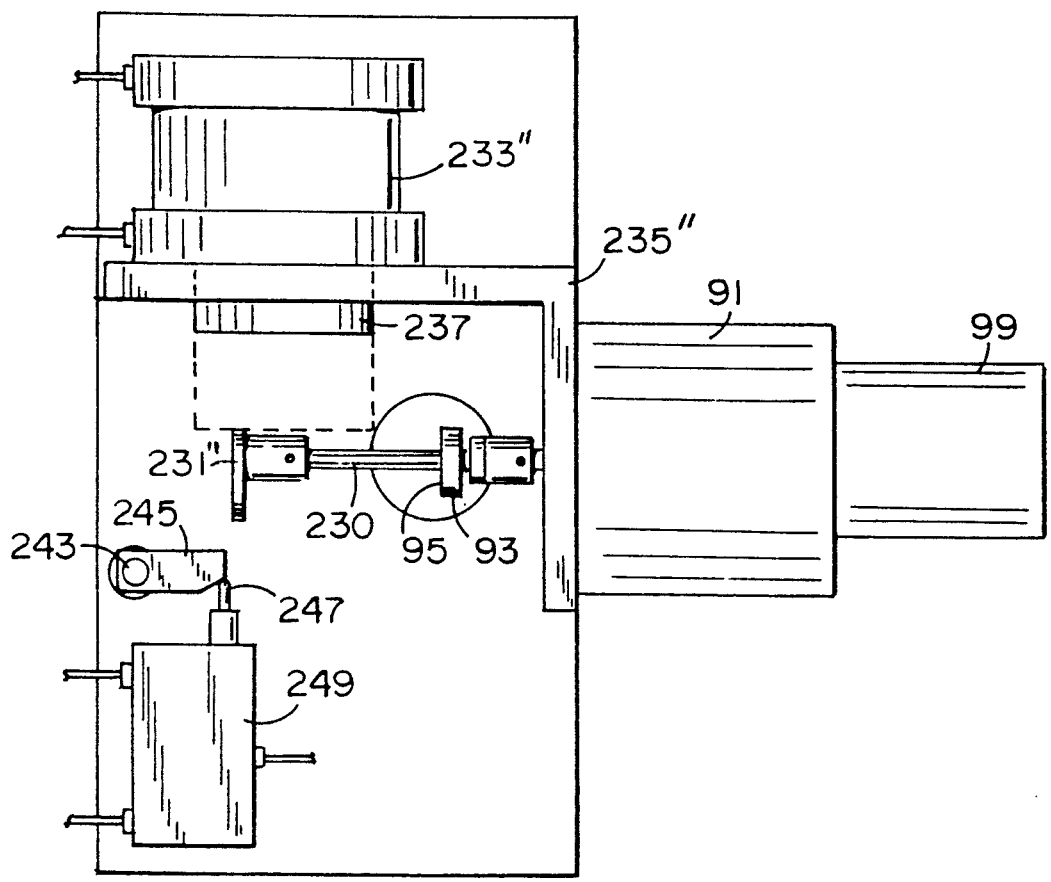
FIG. 16 is an elevational view of the interlock assembly which prevents the crucibles from pouring over the burners.
Figure 17:
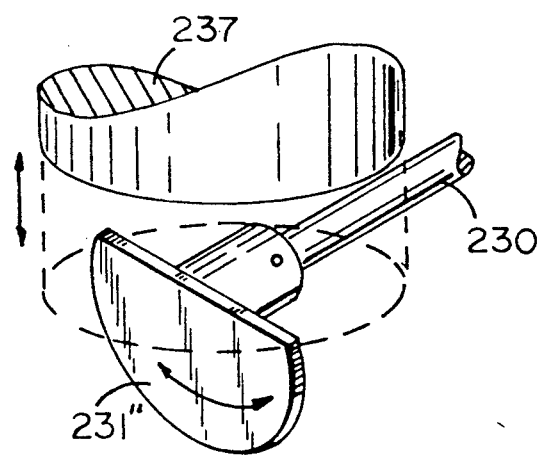
FIG. 17 is an enlarged view of the portion of the interlock circled in FIG. 2.
Figure 18:
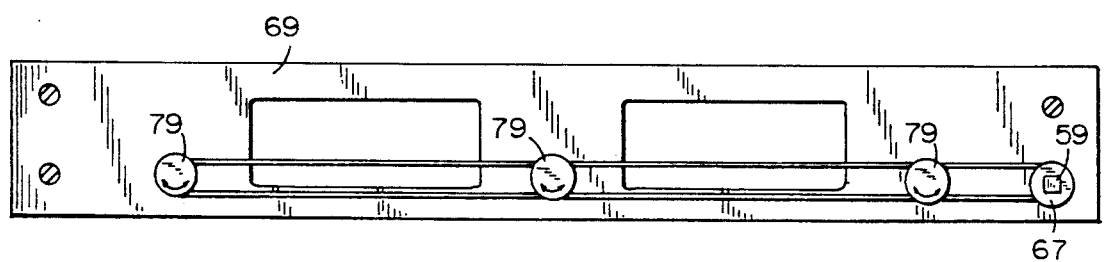
FIG. 18 is a rear view of movable subassembly.

As previously discussed, nothing is added to or poured from the crucible while it is over a burner. Referring to FIG. 16, the interlock circuit is shown which prevents the apparatus used to horizontally rock the crucibles from pouring the contents of a crucible out while it is being heated. As previously discussed, servo motor 91, equipped with shaft encoder 99, controls the horizontal rocking of the crucibles. Servo motor 91 has an output shaft 230 upon which sprocket 95 is mounted.

Figure 2:
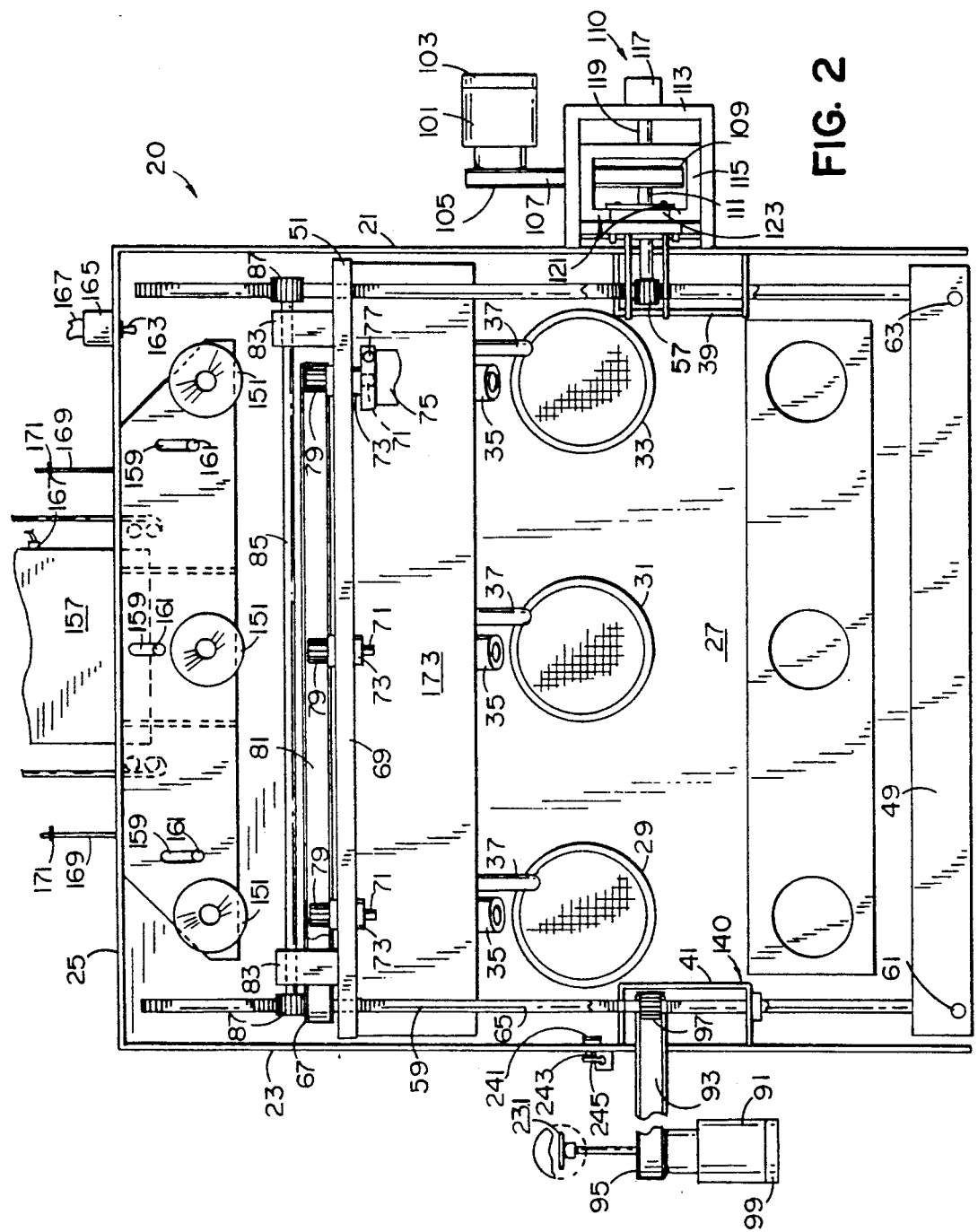
FIG. 2 is a top plan view of the apparatus.
Figure 4:
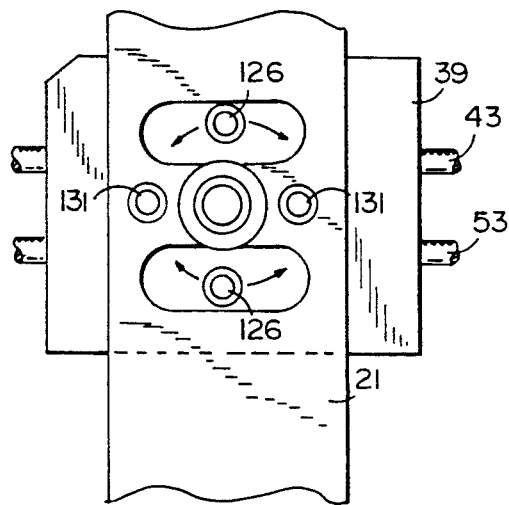
FIG. 4 is an elevational view showing the bushings in the journal block and frame.
Figure 3:
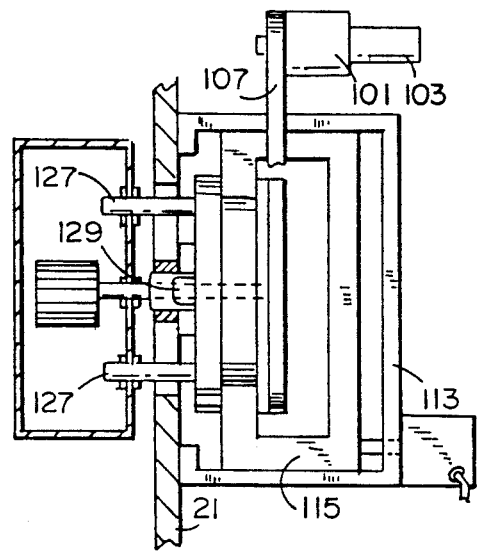
FIG. 3 is a sectional view of the clutch assembly.

Continuous chain 93 is trained over sprocket 95 and connects to gear 97 mounted on square shaft 65 (FIG. 2). On the end of shaft 230, a limit member in the form of a semicircle of metal 231" is mounted. A pneumatic cylinder 233" is mounted on frame 235". Cylinder 233" has a movable piston 237, which extends downwardly above limit member 231. The oscillation of shaft 230 and limit member 231" is controlled by shaft encoder 99 and the control circuitry of the apparatus. The limit member 237 does not come into contact with piston 237 during normal operation. If there is a problem in the control circuitry, and motor 91 attempts a complete revolution which would dump the contents of the crucible into the burner, limit member 91 will strike piston 237 stopping the motor from turning and protecting the burner.

Now referring to FIG. 2, a finger 241 extends downwardly through an aperture in sidewall 23. Finger 241 is connected to a shaft 243 which, in turn, is coupled to an actuating arm 245. When it is time to pour the contents out of the crucible, the main burners are turned off and subassembly 51 moves toward the front of the machine to bring the crucibles to station 180. Front plate 69 of subassembly 51 strikes finger 241 causing arm 245 to press pin 247 on valve 249 which activates pneumatic cylinder 233", causing piston 237 to retract from limit member 231". Motor 91, now under the control of the apparatus electronics, can rotate pouring the contents out of the crucible into the appropriate casting dish or beaker for analysis.

From the above description it can be seen that the main burners of the apparatus are now protected from accidental spills of either the molten material in the crucibles or of any additional materials such as wetting agents which might be added to the crucibles. Also, the mixing pattern of the crucibles is made variable to fit the characteristics of the particular sample by the simple procedure of adjusting the extent of movement of servo motors 91 and 101.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modifications.

The embodiments of the invention in which an exclusive property or privilege is claimed are defined as follows:

1. An electrical resistance heater module for heating a casting dish in a fluxer comprising:
   a frame member;
   an insulating member on said frame member, said insulating member having an upper surface configured for supporting a casting dish;
   a resistive heating element in said insulating member positioned to supply heat to a casting dish supported on said upper surface of said insulating member;
   an electrical conductor supported by and electrically insulated from said frame member for supplying electrical energy to said resistive heating element; and
   a heater module conduit supported by said frame member, said heater conduit including an outwardly extending end connectable to a fluxer conduit which is coupled to a source of cool air external to the fluxer such that the fluxer conduit and said heater conduit supply cooling air to a casting dish on said upper surface of said insulating member to cool the contents of a casting dish when heating is completed, said heater conduit extending through an aperture in said insulating member below the position occupied by a casting dish.

2. An electrical resistance heater module as set forth in claim 1, wherein said insulating member comprises:
   a block of insulating material, said block of insulating material having a first depression in the upper surface thereof for positioning and supporting a casting dish and a second, substantially coaxial, depression for receiving said resistive heating element, said resistive heating element being configured to fit within said second depression.

3. An electrical resistance heater module as set forth in claim 2, wherein said second depression in said block of insulating material has a configured surface for receiving said resistive heating element and for directing the heat from said resistive heating element upwardly while limiting extraneous heating by the bottom and sides of said resistive heating element.

4. An electrical resistance hater module for heating a casting dish in a fluxer comprising:
   a frame member;
   an insulating member on said frame member, said insulating member having an upper surface configured for supporting a casting dish;
   a resistive heating element in said insulating member positioned to supply heat to a casting dish supported on said upper surface of said insulating member;
   an electrical conductor supported by and electrically insulated from said frame member for supplying electrical energy to said resistive heating element; and
   a conduit supported by said frame member for supplying cooling air to a casting dish on said upper surface of said insulating member, said conduit extending through an aperture in said insulating member below the position occupied by a casting dish;
   wherein said frame member comprises:
   a horizontal upper shelf member and a horizontal lower shelf member joined together by a pair of spaced vertical end members to form an open box configuration;
   a sheet of electrical insulating material attached to and covering one side of said box and extending below the bottom member of said box for supporting said box in a raised position; and
   at least one air conduit attached to said lower member and extending downwardly therefrom for supporting said box in a raised position.

5. An electrical resistance heater as set forth in claim 1, wherein said upper and lower shelf members are joined together by end members to form a substantially rectangular box and a sheet of insulating material closes one side of said box and extends below said lower shelf member to form a vertical support for said box, said conduit for supplying cooling air is attached to and extends below said shelf member and provides a vertical support for said box.

6. An electrical resistance heater module as set forth in claim 5, wherein said end connector for said conduit for cooling air is a shaped lower end portion including a circumferential groove adjacent said end portion; and an elastic sealing member is disposed in said circumferential groove for providing an air-tight seal when said conduit is plugged into a suitable socket.

7. An interchangeable heating module for a fluxer, comprising:
a frame;
an insulating member for supporting a receptacle into which a molten sample can be poured for analysis, said insulating member carried on said frame;
a resistive heating element supported by said insulating member;
a conduit extending through said insulating member;
a mechanical connector extending through said frame and coupled to said conduit, said connector removably connecting said module at a predetermined location in a fluxer such that a receptacle supported on said insulating member is positioned for receipt of a molten sample, said connector including a hollow passage which is coupled to said conduit and to a hollow passage in a fluxer associated with a supply of cooling air external to a fluxer when said module is connected to a fluxer, whereby a molten sample in a crucible can be cooled by an external air source after heating by said heating element is completed; and
an electrical connector connectable to a source of electric current supplying said resistive heating element when said module is connected in a fluxer.

8. An interchangeable module as set forth in claim 7, wherein said insulating support is a block of insulating material having an upper surface configured to support said receptacle and a substantially circular depression aligned with and below said configured upper surface for receiving said resistive heating element to enable heat from said resistive heating element to rise out of said depression to contact said receptacle while limiting heat flow in other direction.

9. An interchangeable module as set forth in claim 8, wherein said mechanical connector includes a module conduit with an outwardly extending connector that plugs into a conduit in a fluxer when said module is connected to a fluxer for supplying cooling air to a receptacle, said module conduit extending through an aperture in said block of insulating material.

10. An interchangeable module as set forth in claim 8, wherein said block of insulating material comprises a fibrous ceramic material.

11. An interchangeable module as set forth in claim 7, wherein said resistive heating element comprises molybdenum disilicide.

12. A fluxer comprising:
a housing defining a fluxer enclosure;
a passage through said housing coupled to an air source external to said fluxer enclosure; and
an electric resistance heater module positioned within said fluxer housing, and including:
a frame;
an insulating member carried on said frame for supporting a receptacle within said fluxer enclosure;
a resistive heating element supported on said insulating member;
a conduit extending through said insulating member to a position just below a receptacle;
a connector removably connecting said conduit and said passage, whereby said connector position said module in said fluxer enclosure, and said conduit, said connector and said passage provide an air supply conduit from said external air source through said insulating member for cooling a receptacle after it is heated by said heating elements.

* * * * *

UNITED STATES PATENT AND TRADEMARK OFFICE
CERTIFICATE OF CORRECTION

PATENT NO. : 5,313,047
DATED : May 17, 1994
INVENTOR(S) : O'Brien et al.

It is certified that error appears in the above-indentified patent and that said Letters Patent is hereby corrected as shown below:

Col. 5, line 34;
   "bring" should be --bringing--.

Col. 8, line 41;
   "341" should be --341'--.

Col. 8, line 42;
   "341" should be --341'--.

Col. 8, line 43;
   "341" should be --341'--.

Col. 8, line 44;
   "343 and 345" should be --343' and 345'--.

Col. 8, line 45;
   "347" should be --347'--.

Col. 8, line 47;
   "349" should be --349'--.

Col. 8, line 48;
   "351" should be --351'--.

UNITED STATES PATENT AND TRADEMARK OFFICE
CERTIFICATE OF CORRECTION

PATENT NO.  : 5,313,047
DATED       : May 17, 1994
INVENTOR(S) : O'Brien et al.

It is certified that error appears in the above-indentified patent and that said Letters Patent is hereby corrected as shown below:

Col. 8, line 49;
    "353" should be --353'--.

Col. 8, line 53;
    "355" should be --355'--.

Col. 10, line 57;
    "claim 1" should be --claim 3--.

Signed and Sealed this

Tenth Day of January, 1995

Attest:

BRUCE LEHMAN

Attesting Officer

Commissioner of Patents and Trademarks